United States Patent [19]

Erdmann et al.

[11] Patent Number: 5,209,952
[45] Date of Patent: May 11, 1993

[54] USE OF ORGANOMETALLIC COMPOUNDS TO DEPOSIT THIN FILMS FROM THE GAS PHASE

[75] Inventors: Dietrich Erdmann, Mühltal-Traisa; Ludwig Pohl; Martin Hostalek, both of Darmstadt, all of Fed. Rep. of Germany

[73] Assignee: Merck Patent Gesellschaft Mit Beschraenkter Haftung, Darmstadt, Fed. Rep. of Germany

[21] Appl. No.: 752,697
[22] PCT Filed: Mar. 3, 1990
[86] PCT No.: PCT/EP90/00356
§ 371 Date: Sep. 6, 1991
§ 102(e) Date: Sep. 6, 1991
[87] PCT Pub. No.: WO90/10726
PCT Pub. Date: Sep. 20, 1986

[30] Foreign Application Priority Data
Mar. 9, 1989 [DE] Fed. Rep. of Germany ....... 3907579

[51] Int. Cl.$^5$ .............................................. C23C 16/00
[52] U.S. Cl. ..................................... 427/255.6; 556/1; 556/13; 556/70
[58] Field of Search ......................... 427/248.11, 255.6; 556/1, 13, 70

[56] References Cited

FOREIGN PATENT DOCUMENTS

| 0052979 | 6/1982 | European Pat. Off. . |
| 0251555 | 1/1988 | European Pat. Off. . |
| 0331448 | 9/1989 | European Pat. Off. . |
| 8603228 | 6/1986 | PCT Int'l Appl. . |

OTHER PUBLICATIONS

Mawry, F. et al., *Mass Spectrometric Study of the Pyrolysis of Organometallic Precursors Usable in GaAs Vapor-phase Epitaxy*, Journal of Crystal Growth 91(1988), pp. 97–104.

*Primary Examiner*—Michael Lusigan
*Attorney, Agent, or Firm*—Millen, White, Zelano & Branigan

[57] ABSTRACT

The invention relates to the use of organometallic compounds containing, as metals, aluminum, gallium or indium for the deposition of thin films or epitactic layers from the gas phase.

16 Claims, No Drawings

USE OF ORGANOMETALLIC COMPOUNDS TO DEPOSIT THIN FILMS FROM THE GAS PHASE

SUMMARY OF THE INVENTION

The invention relates to the use of organometallic compounds containing, as metals, aluminum, gallium or indium for the deposition of thin films or epitactic layers from the gas phase.

The deposition of layers of this type from either pure elements of group III or from III-V combinations, such as, for example, gallium arsenide, indium phosphide or gallium phosphide, can be used to produce electrical, electronic, optical and optoelectronic switching elements, compound semiconductors and lasers. The deposition of these layers is effected from the gas phase.

The properties of these films depend on the deposition conditions and on the chemical composition of the deposited film.

All known methods, such as the metal-organic chemical vapor deposition (MOCVD) method, the photo-metal-organic vapor phase (photo-MOVP) method, in which the substances are decomposed by UV irradiation, the laser chemical vapor deposition (laser CVD) method or the metal-organic magnetron sputtering (MOMS) method, are suitable for the deposition from the gas phase. The advantages over other methods are a controllable layer growth, an exact doping control, simple handling due to the standard- or low-pressure conditions, and production friendliness.

In the MOCVD method, organometallic compounds which decompose at a temperature below 1100° C. with deposition of the metal are employed. Typical apparatus currently used for MOCVD comprise a "bubbler" with an inlet for the organometallic component, a reaction chamber which contains the substrate to be coated, and a source for a carrier gas, which should be inert toward the organometallic component. The "bubbler" is kept at a constant, relatively low temperature, which is preferably above the melting point of the organometallic compound, but far below the decomposition temperature. The reaction or decomposition chamber preferably has a much higher temperature which is below 1100° C., at which the organometallic compound decomposes completely and the metal is deposited. The organometallic compound is converted into the vapor state by the carrier gas and flushed into the decomposition chamber with the carrier gas. The mass flow of the vapor can readily be monitored, and controlled growth of the thin layers is thus also possible.

Hitherto, primarily metal alkyls, such as, for example, trimethylaluminum, trimethylaluminum or trimethylindium, have been used for gas-phase deposition. However, these compounds are extremely air sensitive, auto-inflammable and in some cases decompose even at room temperature. Complex safety measures are therefore necessary for the preparation, transport, storage and use of these compounds. Some somewhat more stable adducts of metal alkyls with Lewis bases, such as, for example, trimethylamine and triphenylphosphine, are also known (for example described in GB 2,123,422, EP-A 108,469 or EP-A 176,537), but these are only suitable to a limited extent for gasphase deposition due to the lower vapor pressure. Low vapor pressures are frequently attributable to the presence of dimers, trimers or polymers.

The object of the present invention was to find organometallic compounds which are simple to handle and stable at room temperature and which have a sufficiently high vapor pressure so that they are suitable for the various methods of gas-phase deposition.

It has now been found that organometallic compounds of aluminum, gallium and indium, which contain branched or bulky radicals have a suitable vapor pressure and are thus highly suitable for gas-phase deposition. Similar compounds are known from EP-A 0,295,467. However, the compounds described there are usually dimeric and are therefore again not used for deposition from the gas phase, but instead for deposition from the liquid phase.

The invention thus relates to the use of organometallic compounds of the formula I

$$(R^1)_{3-n}M-Y_n \qquad I$$

in which

M is aluminum, gallium or indium, n is 1, 2 or 3

Y is $-NR^2R^3$, $-PR^2R^3$, $-AsR^2R^3$ or $-SbR^2R^3$, $R^1$, $R^2$, $R^4$ and $R^5$ in each case independently of one another, are H, an alkyl group having 1-8 C atoms, where the alkyl group may be partly or fully fluorinated, a cycloalkyl, alkenyl or cycloalkenyl group, in each case having 3-8 C atoms, or an aryl group, $R^1$ is alternatively 1,2—$(CH_2)_p$—$C_6H_4$—$(CH_2)_q$—Z 1,2—$(CH_2)_p$—$C_6H_{10}$—$(CH_2)_q$—Z, 1,2—$(CH_2)_p$—$C_6H_8$—$(CH_2)_q$—Z, 1,2—$(CH_2)_p$—$C_6H_6$—$(CH_2)_q$—Z, 1,2—$(CH_2)_p$—$C_5H_8$—$(CH_2)_q$—Z, 1,2—$(CH_2)_p$—$C_5H_6$—$(CH_2)_q$—Z, 1,2—$(CH_2)_p$—$C_5H_4$—$(CH_2)_q$—Z, or 1,2—$(CH_2)_p$—$C_4H_6$—$(CH_2)_q$—Z, p and q, in each case independently of one another, are 0, 1, 2 or 3, Z is $-NR^4R^5$, $-PR^4R^5$, $-AsR^4R^5$ or $-SbR^4R^5$ and $R^3$ is a branched alkyl or alkenyl group, in each case having 3-8 C atoms, it being possible for these groups to be partly or fully fluorinated, a cycloalkyl or cycloalkenyl group, in each case having 3-8 C atoms, or an aryl group for the deposition of thin films or layers from the gas phase.

The invention furthermore relates to a process for the preparation of thin films and epitactic layers by gas-phase deposition from organometallic compounds, in which process the organometallic substances employed are compounds of the formula I. The invention furthermore comprises, in the process according to the invention for the preparation of, for example, compound semiconductors, adding, during the deposition process, one or more arsenic, antimony or phosphorus compounds which are gaseous under the reaction conditions used.

The compounds of the formula I are stabilized intramolecularly by electron transfer from the nitrogen, phosphorus, arsenic or antimony atom to the electron-deficient III B element. They are therefore stable toward air and oxygen, no longer auto-inflammable and thus easy to handle.

In the gas phase, however, the compounds according to the invention can easily be decomposed with deposition of the metal. Since the compounds of the formula I contain stable and readily removable leaving groups, the result is less incorporation of carbon, which has great advantages for the quality of the end products.

The deposited films can be formed both from the pure III B element and from combination with elements of group V on any desired substrates. Depending on the substrate and deposition technique, they can have an epitactic nature.

Compounds of the formula I which, due to branched or bulky radicals, are in monomeric form and therefore have a higher vapor pressure are very particularly preferred and highly suitable for the MOCVD technique.

In the formula I, M is aluminum (Al), Gallium (Ga) or Indium (In), preferably Ga or In.

Y is primarily preferably —$NR^2R^3$, and secondarily preferably —$PR^2R^3$ or —$AsR^2R^3$.

n is preferably 1.

In the formula I, the radicals $R^1$, $R^2$, $R^4$ and $R^5$ are preferably each a straight-chain or branched alkyl group having 1–8 C atoms, preferably having 1–5 C atoms. The alkyl groups are preferably straight-chain and are accordingly preferably methyl, ethyl, propyl, butyl, pentyl, furthermore also hexyl, heptyl, octyl, isopropyl, sec.-butyl, tert.-butyl, 2-methylpentyl, 3-methylpentyl or 2-octyl. The alkyl radicals may be partly or alternatively fully fluorinated and are, for example, monofluoromethyl, difluoromethyl, trifluoromethyl, difluoroethyl, trifluoroethyl, pentafluoroethyl or trifluoropropyl. Preferably, only one of the radicals $R^1$, $R^4$ or $R^5$ is H.

If $R^1$, $R^2$, $R^4$ and/or $R^5$ are a cycloalkyl or cycloalkenyl group having 3–8 C atoms, they are preferably cyclopropyl, cyclobutyl, cyclopentyl, cyclopentenyl, cyclohexyl, cyclohexenyl, cyclohexadienyl, cycloheptyl, cycloheptenyl, cycloheptadienyl, cyclooctyl, cyclooctenyl, cyclooctadienyl, cyclooctatrienyl or cyclooctatetraenyl.

$R^1$, $R^2$, $R^4$ and/or $R^5$ are preferably alternatively alkenyl groups having 3–8 C atoms, preferably having 3–5 C atoms. Accordingly, they are preferably propenyl, butenyl, pentenyl, or furthermore hexenyl, heptenyl or octenyl.

In addition, preferred compounds of the formula I are those in which $R^1$, $R^2$, $R^4$ and/or $R^5$ are aryl groups. Aryl group is preferably a phenyl group. This phenyl group may also be substituted. Since these substituents exert no significant influence on the intended use, all substituents which have no adverse effect on the decomposition reaction are allowed.

The radical $R^1$ may occur more than once and may then be different or the same.

In the formula I, $R^1$ may also be 1,2—$(CH_2)_p$—$C_6H_4$—$(CH_2)_q$—Z, 1,2—$(CH_2)_p$—$C_6H_{10}$—$(CH_2)_q$—Z, 1,2—$(CH_2)_p$—$C_6H_8$—$(CH_2)_q$—Z, 1,2—$(CH_2)_p$—$C_6H_6$—$(CH_2)_q$—Z, 1,2—$(CH_2)_p$—$C_5H_8$—$(CH_2)_q$—Z, 1,2—$(CH_2)_p$—$C_5H_6$—$(CH_2)_q$—Z, 1,2—$(CH_2)_p$—$C_5H_4$—$(CH_2)_q$—Z, or 1 2—$(CH_2)_p$—$C_4H_6$—$(CH_2)_q$—Z, in which Z is preferably —$NR^4R^5$ or —$AsR^4R^5$, and p and q are each preferably 0, 1 or 2.

Accordingly, the following groups (1)-(9) are particularly preferred for $R^1$:

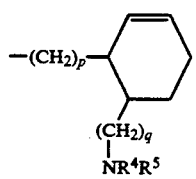

(1)

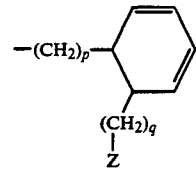

(2)

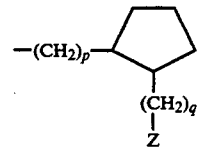

(3)

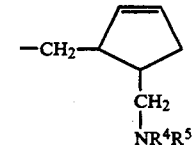

(4)

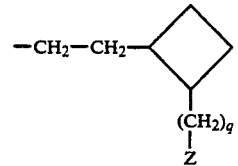

(5)

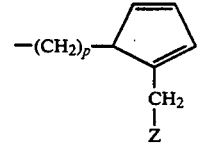

(6)

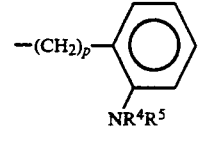

(7)

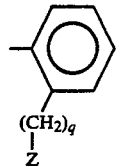

(8)

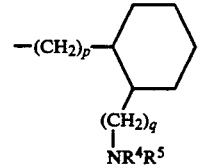

(9)

In the formula I, $R^3$ is preferably a branched alkyl group having 3–8 C atoms, preferably having 3–4 C atoms, which may also be partly or fully fluorinated. Accordingly, $R^3$ is preferably iso-propyl, sec.-butyl, tert.-butyl, 1- methylbutyl, 2-methylbutyl, 1,2-dimethylpropyl, furthermore also 2-methylpentyl, 3- methylpentyl, 2- octyl or 2- hexyl.

If R³ is a cycloalkyl or cycloalkenyl group, groups which are also indicated as preferred for R¹, R², R⁴ and R⁵ are preferred.

The compounds of the formula I thus always contain at least one bulky ligand, in the form of a branched group or a cyclic radical. Compounds in which R² and R³ are branched alkyl groups are preferred here.

The following compounds are, for example, preferred representatives of the compounds of the formula I:

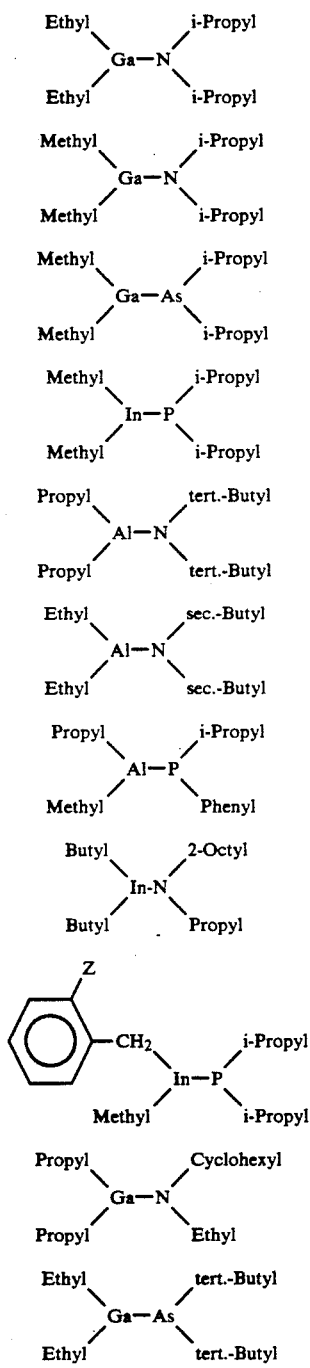

The compounds of the formula I are highly suitable for MOCVD epitaxy or the MOCVD method since they decompose at relatively high temperatures with liberation of the corresponding metal. They are likewise suitable for the other methods of gas-phase deposition, such as photo-MOVP, laser CVD or MOMS.

The compounds of the formulae I are prepared by methods known per se, as described in the literature (for example, G. Bähr, P. Burba, Methoden der organischen Chemie, Volume XIII/4, Georg Thieme Verlag, Stuttgart (1970)), more precisely under reaction conditions which are known and are suitable for the reactions mentioned. Use can also be made here of variants which are known per se, but not described here in greater detail.

Thus, compounds of the formula I can be prepared, for example, by reacting metal alkyl chlorides with an alkali metal organyl of the appropriate Lewis base or of a Grignard compound in an inert solvent.

The reactions are preferably carried out in inert solvents. Suitable solvents here are all solvents which do not interfere with the reaction and do not participate in the reaction proceedings. The reaction temperatures essentially correspond to those which are known from the literature for the preparation of similar compounds.

In the process according to the invention for the preparation of thin films or epitactic layers on any desired substrates, the starting compounds employed in the gasphase deposition processes, known per se, of organometallic compounds are the stabilized organometallic compounds of the formula I. The reaction conditions can be selected analogously to the values known from the literature and known to those skilled in the art.

To produce compound semiconductors and electronic and optoelectronic components, one or more arsenic, antimony or phosphorus compounds which are gaseous under the reaction conditions used, for example $AsH_3$, $As(CH_3)$, $PH_3$ or $SbH_3$, may additionally be added to the decomposition chamber during the deposition process in the process according to the invention. A further variant of the process according to the invention comprises additionally adding dope to the organometallic compounds of the formula I according to the invention during the deposition process. The dopes employed here are volatile organometallic compounds of iron, magnesium, zinc or chromium. Examples of preferred compounds here are $Zn(CH_3)_2$, $Mg(CH_3)_2$ or $Fe(C_5H_5)_2$.

It is furthermore possible to add the compounds of the formula I as dopes to other organometallic compounds during the deposition process.

The layers produced by the process according to the invention can be used for the production of electronic, electric, optical and optoelectronic switching elements, compound semiconductors or lasers.

Since, for thermodynamic reasons, only about 1–10% of the free metal alkyls employed can be deposited as an epitaxial layer on the substrate in the epitaxy equipment currently employed, the destruction of excess metal alkyls, which, due to their extreme sensitivity, cannot be recovered, is a considerable problem. By contrast, the compounds of the formula I according to the invention, due to their high stability, open up new opportunities for hazard-free destruction or recovery of the valuable III B compounds.

EXAMPLES

The examples below are intended to illustrate the invention in greater detail. Temperature data are always given in degrees Celsius. M.P. denotes melting point and B.P. denotes boiling point.

EXAMPLE 1

10.6 g (0.064 mol) of diethylgallium chloride (Et$_2$GaCl) are added over the course of one hour to a mixture of 6.9 g (0.064 mol) of lithium diisopropylamide (iPr$_2$N-Li) and 80 ml of hexane. Hexane is removed by distillation, and the product Et$_2$Ga-N iPr$_2$ is subjected to fractional distillation in vacuo.

B.P.=42° C./0.6 mbar $^1$NMR spectrum ($\delta$ values in ppm); 250 MHz:

0 Ethyl groups: 0.82 (q, 4H), 1.66 (tr, 6H)

iPr$_2$N group: 1 05 (d, 12H); 3.05 (m, 2H).

EXAMPLE 2

28.8 g (0.16 mol) of dimethylindium chloride are added over the course of one hour to a mixture of 17.5 g (0.16 mol) of lithium diisopropylamide (iPr$_2$N-Li) and 150 ml of hexane. The hexane is removed by distillation, and the product Me$_2$In-NiPr$_2$ is subjected to fractional distillation in vacuo.

$^1$H NMR spectrum (& values in ppm); 250 MHz:

Methyl groups: 0.2 (s, 6H)

iPr$_2$N group: 1.0 (d, 12H); 2.85 (m, 2H)

We claim:

1. In a process for the deposition of epitactic layers employing an organometallic compound for the deposition of thin films or layers form the gas phase, the improvement comprising said organometallic compound being a compound of formula I

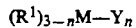  I, wherein

M is aluminum, alllium or indium;

n is 1, 2 or 3;

Y is —NR$^2$R$^3$, —RP$^2$R$^3$, —ASR$^2$R$^3$;

R$^1$, R$^2$, R$^4$ and R$^5$, in each case independently of one another, are H, an alkyl group having 1-8 C atoms, where the alkyl group may be partly or fully fluorinated, a cycloalkyl, alkenyl or cycloalkenyl group, in each case having 3-8 C atoms, or an aryl group, R$^1$ is alternatively 1,2—(CH$_2$)$_p$—C$_6$H$_4$—(CH$_2$)$_q$—Z, 1,2—(CH$_2$)$_p$—C$_6$H$_{10}$—(CH$_2$)$_q$—Z, 1,2—(CH$_2$)$_p$—C$_6$H$_8$—(CH$_2$)$_q$—Z, 1,2—(CH$_2$)$_p$—C$_6$H$_6$—(CH$_2$)$_q$—Z, 1,2—(CH$_2$)$_p$—C$_5$H$_8$—(CH$_2$)$_q$—Z, 1,2—(CH$_2$)$_p$—C$_5$H$_6$—(CH$_2$)$_q$—Z, 1,2—(CH$_2$)$_p$—C$_5$H$_4$—(CH$_2$)$_q$—Z, or 1,2—(CH$_2$)$_p$—C$_4$H$_6$—(CH$_2$)$_q$—Z;

p and q, in each case independently of one another, are 0, 1, 2 or 3;

Z is —NR$^4$R$^5$, —PR$^4$R$^5$, —AsR$^4$R$^5$ or —SbR$^4$R$^5$; and is a branched alkyl or alkenyl group, in each case having 3-8 C atoms, it being possible for these groups to be partly or fully fluorinated, a cycloalkyl or cycloalkenyl group, in each case having 3,-8 C atoms, or an aryl group.

2. A process according to claim 1, for the deposition of epitactic layers.

3. In a process for the preparation of thin films on substrates by gas-phase deposition from an organometallic compounds, the improvement comprising said organometallic compound being a compound of formula I

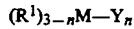  I, wherein

M is aluminum, gallium or indium;

n is 1, 2 or 3;

is —NR$^2$R$^3$, —PR$^2$R$^3$, —AsR$^2$R$^3$ or —SbR$^2$R$^3$;

R$^1$, R$^2$, R$^4$ and R$^5$, in each case independently of one another, are H, an alkyl group having 1-8 C atoms, where the alkyl group may be partly or fully fluorinated, a cycloalkyl, alkenyl or cycloalkenyl group, in each case having 3-8 C atoms, or an aryl group, R$^1$ is alternatively 1,2—(CH$_2$)$_p$—C$_6$H$_4$—(CH$_2$)$_q$—Z, 1,2—(CH$_2$)$_p$—C$_6$H$_{10}$—(CH$_2$)$_q$—Z, 1,2—(CH$_2$)$_p$—C$_6$H$_8$—(CH$_2$)$_q$—Z, 1,2—(CH$_2$)$_p$—C$_6$H$_6$—(CH$_2$)$_q$—Z, 1,2—(CH$_2$)$_p$—C$_5$H$_8$—(CH$_2$)$_q$—Z, 1,2—(CH$_2$)$_p$—C$_5$H$_6$—(CH$_2$)$_q$—Z, 1,2—(CH$_2$)$_p$—C$_5$H$_4$—(CH$_2$)$_q$—Z, 1,2—(CH$_2$)$_p$—C$_4$H$_6$—(CH$_2$)$_q$—Z;

p and q, in each case independently of one another, are 0, 1, 2 or 3;

is —NR$^4$R$^5$, —PR$^4$R$^5$, —AsR$^4$R$^5$ or —SbR$^4$R$^5$; and is a branch alkyl or alkenyl group, in each case having 3-8 C atoms, it being possible for these groups to be partly or fully fluorinated, a cycloalkyl or cycloalkenyl group, in each case having 3-8 C atoms, or an aryl group.

4. A process according to claim 3, wherein, to produce compound semiconductors, electric, electronic, optical or optoelectronic components, one or more arsenic, antimony or phosphorus compounds in which are gaseous under the reaction conditions used are additionally added during the deposition process.

5. A process according to claim 3, wherein, in addition to the organometallic compounds of formula I, dopes are added during the deposition process.

6. A process according to claim 3, wherein the compounds of formula I are added during the deposition process of other organometallic compounds.

7. A process according to claim 3, wherein M is gallium or indium.

8. A process according to claim 3, wherein Y is —NR$^2$R$^3$.

9. A process according to claim 3, wherein Y is —PR$^2$R$^3$ or —AsR$^2$R$^3$.

10. A process according to claim 3, wherein n is 1.

11. A process according to claim 3, wherein M is gallium or indium; Y is —NR$^2$R$^3$, PR$^2$R$^3$, PR$^2$R$^3$, or —AsR$^2$R$^3$; and n is 1.

12. A process according to claim 3, wherein is 1,2—(CH$_2$)$_p$—C$_6$H$_4$—(CH$_2$)$_q$—Z, 1,2—(CH$_2$)$_p$—C$_6$H$_{10}$—(CH$_2$)$_q$—Z, 1,2—(CH$_2$)$_p$—C$_6$H$_8$—(CH$_2$)$_q$—Z, 1,2—(CH$_2$)$_p$—C$_6$H$_6$—(CH$_2$)$_q$—Z, 1,2—(CH$_2$)$_p$—C$_5$H$_8$—(CH$_2$)$_q$—Z, 1,2—(CH$_2$)$_p$—C$_5$H$_6$—(CH$_2$)$_q$—Z, 1,2—(CH$_2$)$_p$—C$_5$H$_4$—(CH$_2$)$_q$—Z, or 1,2—(CH$_2$)$_p$—C$_4$H$_6$—(CH$_2$)$_q$—Z;

Z is —NR$^4$R$^5$ or —AsR$^4$R$^5$; and p and q are each independently 0, 1, or 2.

13. A process according to claim 1, wherein R$^1$ is

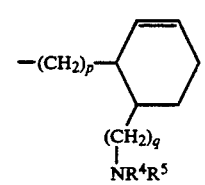  (1)

-continued (2) 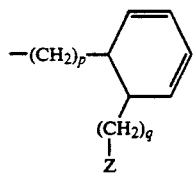

(3) 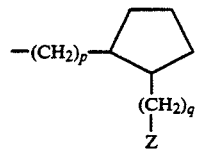

(4) 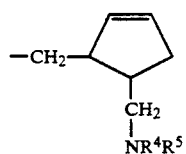

(5) 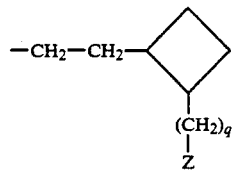

-continued (6) 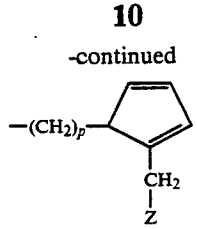

(7) 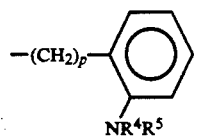

(8) 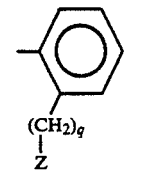

or (9) 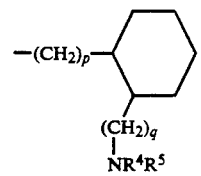

14. A process according to claim 3, wherein $R^3$ is a branched alkyl group having 3-8 C atoms.

15. A process according to claim 3, wherein $R^1$ and $R^2$, are each a straight-chain or branched alkyl group having $C_1$-$C_8$ atoms which are optionally partly or fully fluorinated.

16. A process according to claim 12, wherein $R^2$ is a straight-chain or branched alkyl group having $C_1$-$C_8$ atoms which is optionally partly or fully fluorinated.

* * * * *

UNITED STATES PATENT AND TRADEMARK OFFICE
CERTIFICATE OF CORRECTION

PATENT NO. : 5,209,952
DATED : May 11, 1993
INVENTOR(S) : Dietrich ERDMANN

It is certified that error appears in the above-indentified patent and that said Letters Patent is hereby corrected as shown below:

Claim 3; Col. 8; Line 2:

Reads -- (is $- NR^2R^3$, $-PR^2R^3$, $-AsR^2R^3$ or $-SbR^2R^{3'}$)

Should read -- Y is $-NR^2R^3$, $-PR^2R^3$, $-AsR^2R^3$ or $-SbR^2R^3$, --

Signed and Sealed this

Fourth Day of January, 1994

*Attest:*

BRUCE LEHMAN

*Attesting Officer*  Commissioner of Patents and Trademarks